(12) United States Patent
Hilaire et al.

(10) Patent No.: US 6,171,279 B1
(45) Date of Patent: *Jan. 9, 2001

(54) OVER-THE-WIRE DILATATION CATHETER

(75) Inventors: Pierre Hilaire, Paris; Philippe Salbert, Domont, both of (FR)

(73) Assignee: CathNet-Science S.A., Paris (FR)

( * ) Notice: Under 35 U.S.C. 154(b), the term of this patent shall be extended for 0 days.

This patent is subject to a terminal disclaimer.

(21) Appl. No.: 08/967,202

(22) Filed: Oct. 29, 1997

Related U.S. Application Data

(63) Continuation of application No. 08/522,672, filed on Sep. 1, 1995, now abandoned.

(30) Foreign Application Priority Data

Jul. 6, 1995 (FR) .................................................. 95 08175

(51) Int. Cl.[7] .................................................. A61M 29/00
(52) U.S. Cl. .................. 604/96.01; 604/103.09; 606/192; 600/433
(58) Field of Search ............................ 604/96, 102, 103, 604/104, 264, 523, 524, 525, 526, 528, 530, 532, 533; 606/192, 193, 194; 600/433–435, 585

(56) References Cited

U.S. PATENT DOCUMENTS

| 5,176,637 | * | 1/1993 | Sagae | 606/192 |
|---|---|---|---|---|
| 5,320,605 | * | 6/1994 | Sahota | 606/194 |
| 5,425,711 | * | 6/1995 | Ressemann et al. | 606/194 |
| 5,490,837 | * | 2/1996 | Blaeser et al. | 606/194 |
| 5,520,647 | * | 5/1996 | Solar | 604/102 |
| 5,531,690 | * | 7/1996 | Solar | 604/282 |
| 5,542,926 | * | 8/1996 | Crocker | 604/102 |
| 5,545,134 | * | 8/1996 | Hilaire et al. | 604/282 |
| 5,545,138 | * | 8/1996 | Fugoso et al. | 604/102 |
| 5,549,552 | * | 8/1996 | Peters et al. | 606/194 |
| 5,607,394 | * | 3/1997 | Andersen et al. | 604/102 |

* cited by examiner

*Primary Examiner*—John G. Weiss
*Assistant Examiner*—LoAn H. Thanh
(74) *Attorney, Agent, or Firm*—James J. Leary; Carol D. Titus

(57) ABSTRACT

The present invention relates to an "over-the-wire" dilatation catheter of the type comprising a flexible tubular body having a distal part, an intermediate part and a proximal part.

According to the invention, the body comprises a core having a high modulus of elasticity, which core is permanently joined at one end to the proximal part and embedded at its other end in a wall defining an inner duct for a guide-wire to pass through.

The invention finds a particular application in the treatment of stenoses of blood vessels.

20 Claims, 1 Drawing Sheet

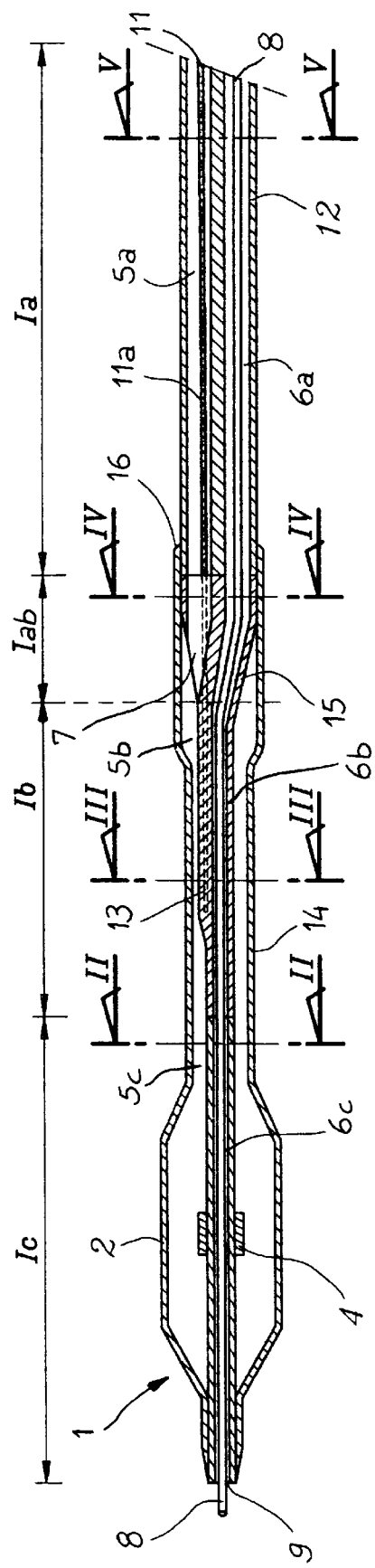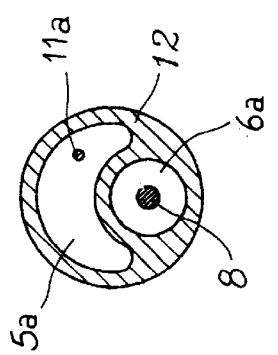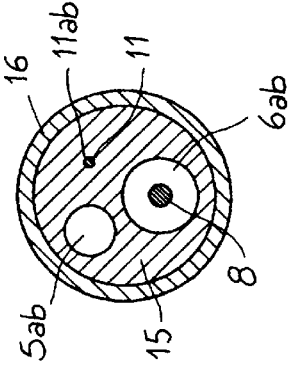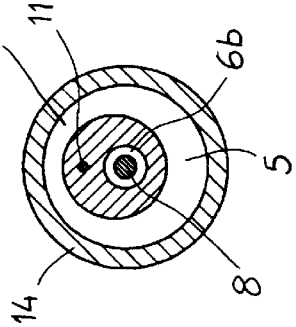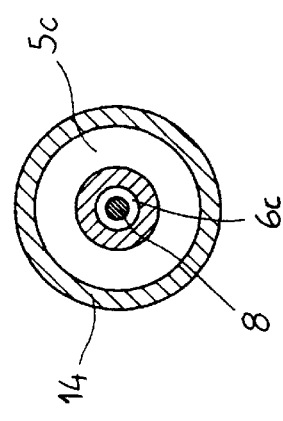

OVER-THE-WIRE DILATATION CATHETER

This application is a continuation of application Ser. No. 08/522,672, filed on Sep. 1, 1995, now abandoned.

FIELD OF THE INVENTION

The present invention relates to a dilatation catheter of the type known as "over the wire" for introduction into a body canal such as for example a blood vessel.

The invention is principally applicable to the treatment of disorders of the coronary arteries but it can also be used for treating disorders of other body canals, for example the oesophagus or the urethra.

BACKGROUND OF THE INVENTION

Such disorders are generally provoked by the presence, on the inner walls of the canal, of deposits causing strictures or stenoses in said canal.

The treatment of such disorders generally calls for the use of a dilatation catheter for restoring the normal flowing section of the canal at the level of the stenosis by compression with the aid of a balloon.

A guide, normally produced in the form of a wire is used for helping the catheter to reach the stenosis.

The guide-wire is generally longer than the catheter, typically by about 20 to 50 cm, in order to urge the catheter forward into the body canal, by sliding it along the wire.

For correctly positioning the balloon at the level of the stenosis, it is necessary to bring the distal end of the catheter to beyond said stenosis.

Understandably, for the catheter to pass through the stenosis, it is generally necessary to apply a thrusting pressure on the latter.

Said thrusting pressure is exerted by the practitioner at the level of the proximal end of the catheter.

Transmission of said thrusting pressure to the distal end of the catheter raises a problem which, heretofore, has not been solved satisfactorily.

SUMMARY OF THE INVENTION

In the circumstances, it is the object of the present invention to solve the technical problem consisting in providing a new design of dilatation catheter called "over the wire" which can be readily produced on an industrial scale, which is easy to use, and which enables an efficient transmission to the distal part comprising the balloon, of the thrusting pressure exerted at the level of the proximal part.

The solution provided by the present invention for solving said technical problem consists in an over-the-wire dilatation catheter of the type comprising:
  a flexible tubular body comprising a distal part, an intermediate part and a proximal part, and having:
  a radially deformable portion forming a balloon, disposed at the level of its distal part;
  a first inner duct fluidly connected at one end to the interior of the balloon, in liquidtight manner, and connected at the other end to a fluid supply source in order to enable inflating and deflating of the balloon;
  a second inner duct, which does not communicate with said first inner duct and traverses longitudinally the body, said duct being defined by a substantially tubular wall and adapted to allow the passage of a guide-wire, characterized in that said catheter further comprises a core having a high modulus of elasticity and being permanently joined to the body by its proximal end and of which the distal end is embedded in the wall defining said second inner duct at the level of its intermediate part.

The novelty of the present invention therefore resides in the use of an element intended for rigidifying the body of the catheter, and for ensuring a reliable and safe transmission of the thrusting pressure exerted at the level of the proximal part of the catheter up to the level of its distal part.

According to an advantageous characteristic, the body comprises in its proximal part a two-channel tube constituted of the eccentric proximal portion of the second inner duct and of a substantially semi-spherical channel forming the proximal part of the first inner duct inside which the free proximal section of said core is contained.

According to another characteristic, the body comprises, in the transitional zone between its proximal part and its intermediate part, a three-channel tube, constituted of a first upper channel, extending, from on the one hand, the semi-cylindrical channel of the proximal part, and on the other hand, connecting to the intermediate portion of the first inner duct, of a second lower channel communicating on each side of the transitional zone with, respectively, the proximal and intermediate portions of the second inner duct, and of a third channel inside which the corresponding section of the metallic core is confined.

According to yet another characteristic, the body comprises, in its intermediate part, an outer tube that extends from the radially deformable balloon-forming portion of the distal part and that surrounds coaxially the intermediate part of the second inner duct while providing an annular space which forms the intermediate part of the first inner duct.

Preferably, the outer tube is fixed at its proximal end to the three-channel tube and to the two-channel tube.

As the core is embedded in the wall of said second inner duct, there is no noticeable reduction of the flowing section of the fluid used for inflating the balloon. Such configuration therefore does not in any way reduce the balloon inflating and deflating time.

According to a particular characteristic, said core has a cross-section which is decreasing from its proximal end towards its distal end.

The gradual decrease of the cross-section of the core therefore confers to the catheter assembly a progressive flexibility under bending and prevents all risks of breaking or kinking thereof.

The resulting catheter shows relatively high rigidity in its proximal part, and a certain amount of flexibility in its distal part, the passage from the rigid part to the more flexible part being done without any breaking.

In other words, the catheter according to the present invention comprises a sufficiently rigid body to allow a good transmission towards the distal part, of the thrusting pressure exerted on the proximal part while ensuring sufficient flexibility at the level of said distal part to enable easy maneuverability of the catheter particularly in the bent portions of the body canal.

The terms "with high modulus of elasticity" as used within the present description and claims, are meant to cover any materials having a modulus of elasticity of at least 10000 MPa.

Advantageously, said core is produced in a metallic material, preferably steel.

According to another characteristic of the invention, said core extends in the intermediate part up to a point situated upstream and in the immediate vicinity of the balloon-forming portion.

Such particular configuration prevents all risks of the balloon being perforated by said core while making sure that the thrusting pressure is transmitted up to the stenosis.

BRIEF DESCRIPTION OF THE DRAWINGS

The invention will be more readily understood, and other characteristics and advantages thereof will emerge from the following description of a currently preferred embodiment of the invention, given with reference to the accompanying drawings, in which:

FIG. 1 is a view of a longitudinal section of a so called "over-the-wire" dilatation catheter according to the present invention, FIG. 2 is a cross-sectional view along line II—II of FIG. 1, FIG. 3 is a cross-sectional view along line III—III of FIG. 1, FIG. 4 is a cross-sectional view along line IV—IV of FIG. 1, FIG. 5 is a cross-sectional view along line V—V of FIG. 1,

DETAILED DESCRIPTION OF A PREFERRED EMBODIMENT

In the following description, the body canal selected by way of example is a blood vessel not shown, such as in particular a coronary artery.

FIG. 1 thus diagrammatically illustrates a dilatation catheter of the over-the wire type according to the invention.

Said catheter comprises a flexible tubular body 1 having a proximal part 1a, an intermediate part 1b and a distal part 1c.

By way of example, for a catheter having a total length of 135 cm, the proximal part 1a may have a length of about 111 cm, the intermediate part 1b a length of about 21 cm and the distal part 1c a length of about 3 cm.

Preferably, the flexible tubular body 1 has a cross-section which is substantially circular and constant throughout most of its length.

The body 1 is provided at the level of its distal part 1c with a radially deformable portion 2 forming balloon, and at the level of its proximal part 1a, with a multi-channel tubular portion 12, enabling connection to a fluid-supply source to allow inflating and deflating of the balloon 2 and passage of a guide-wire 8 traversing longitudinally the body 1.

The flexible body 1 may be produced for example from one or more semi-rigid thermoplastic materials selected among the polyethylenes, polyamides or even copolymers of PEBAX® or HYTREL® type.

The radially deformable balloon-forming portion 2 may be integrated to the flexible body 1, such as in the illustrated example, or fixed thereon in liquidtight manner by conventional means such as for example heat-sealing or an adhesive. Said portion may also be produced from a thermoplastic material such as for example a polyamide, a polyethylene or even a polyester.

In the drawings, the balloon-forming portion is shown in inflated state.

For easy positioning of the balloon 2 at the level of the stenosis, i.e. before inflating, the body 1 may be equipped with identification means such as for example a radiopaque metallic ring 4; such radiopaque ring may be produced in a metal such as gold, platinum, tungsten or alloys thereof.

Generally speaking, the flexible body 1 comprises a first inner duct 5, extending substantially longitudinally in the distal part 1c, and extending at the level of the intermediate part 1b and of the proximal part 1a.

The flexible body 1 further comprises a second inner duct 6, non-communicating with the first inner duct 5, which also passes through the distal part 1c, the intermediate part 1b and the proximal part 1a, the distal part 5c of the first inner duct 5 fluidly connected to the balloon 2, in liquidtight manner, and its proximal end 5a being connected, via the multi-channel tube 12 to a fluid supply source, not shown, to allow inflating and deflating of the balloon 2.

In the illustrated example, the multi-channel tube 12 is a two-channel tube.

The second inner duct 6 is defined by a substantially tubular wall to be described hereinafter in more details, and is so adapted as to allow the passage of a guide-wire 8 emerging at the distal end of the catheter via an opening 9 provided to this effect. The guide-wire 8, normally in metal, may be introduced in the catheter by grasping its proximal end and threading the guide wire 8 forward into the second inner duct 6 from the catheter base, not shown, up to the distal opening 9.

In the currently preferred embodiment illustrated in FIG. 1, the inner ducts 5 and 6 extend substantially longitudinally inside the body 1 and are coaxial in the distal part 1c and in at least the intermediate part 1b. The proximal part 1a and distal part 1c are interconnected in liquidtight manner by the intermediate part 1b.

The body 1 further comprises a core 11 having a high modulus of elasticity, which core is permanently joined by its proximal end to the body 1, for example by being sealed there on, and of which the distal end 13 is embedded in the wall defining the intermediate portion 6b of the second inner duct 6.

The core 11 has a cross-section which is, for example, circular, and which decreases from its proximal end towards its distal end 13.

The distal end 13 is situated in the immediate vicinity and upstream of said balloon-forming portion 2 with respect to the direction of injection of the inflating fluid.

As can be seen in FIG. 1, the wall defining the radially deformable distal part forming the balloon 2 is extended by an outer tube 14 that extends over the intermediate part 1b. The outer tube 14 coaxially surrounds the central intermediate part 6b of the second inner duct 6 while providing an annular space which forms the intermediate part 5b of the inner duct 5.

Said intermediate part 5b as well as the distal part 5c fluidly connecting to the balloon 2 constitute peripheral inner ducts.

The proximal part 1a of the body 1 is constituted by a two-channel tube 12. Said two-channel tube is constituted, as shown in FIG. 5, of the proximal part 5a of the first inner duct 5 inside which the free proximal section of the core 11a is contained, and of the proximal part 6a of the second inner duct 6 into which the guide-wire 8 is introduced. The part 5a of the first duct 5 is moreover connected to a fluid supply source, not shown, in order to allow inflating and deflating of the balloon 2. The proximal part 6a of the second inner duct 6 is eccentric in order to release a substantially semi-cylindrical or cross-sectionally crescent-shaped channel forming the proximal part 5a of the first inner duct 5.

The second inner duct 6c that is coaxial relatively to the outer tube 14 in the distal part 1c and the intermediate part 1b is produced by stretching a multi-channel tube 15 on the distal side.

In the illustrated example, the tube 15 is a three-channel tube that extends solely in the transitional zone 1*ab* between the intermediate part 1*b* and the proximal part 1*a*. The cross-section of the tube 15 varies continously from one end of the transitional zone 1*ab* to the other, due to the stretching.

As shown in FIG. 4, said tube 15 comprises a first upper channel 5*ab* of substantially circular cross-section, which, on the one hand, extends from the semi-cylindrical channel 5*a* of the proximal part 1*a*, and on the other hand, connects to the intermediate part 5*b* of the first inner duct 5. The tube 15 further comprises a second lower channel 6*ab* communicating, on both sides of the transitional zone 1*ab* with, respectively, the proximal portion 6*a* and the intermediate portion 6*b* of the second inner duct 6 as well as a third channel 11*ab* inside which the corresponding portion of the metallic core 11 is confined.

Beyond the stretched transitional zone 1*ab*, the third channel 11*ab* disappears and the metallic core 11 is then embedded in the wall of the intermediate part 6*b* of the second inner duct 6, as illustrated in FIGS. 1 and 3. Optionally, said wall may be slightly thicker in that area.

The outer tube 14 is fixed by its proximal end 16 to the two-channel tube 15, preferably by heat-sealing.

An opening 7 is made at the level of the narrowing portion in the first upper channel 5*ab* of the three-channel tube 15 so as to constitute a passageway for the fluid intended for inflating and deflating the balloon 2.

Referring to FIG. 1, this shows that the connection between the intermediate part 1*b* and the proximal part 1*a* of a dilatation catheter according to the invention, is achieved by placing in contact and sealing the tubes 15 and 12 previously arranged so as to make the different ducts coincide one with the other. The resulting connection is liquidtight.

The operation and use of the dilatation catheter of the type called "over-the-wire" described hereinabove is in conformity with those described in the prior art to which the man skilled in the art can refer.

In general, a guiding catheter is first introduced in the patient's vessel.

Then, a dilatation catheter according to the present invention, of preselected suitable size and a guide-wire 8 are introduced into said guiding catheter by initially inserting the guide-wire up to the stenosis, and then advancing the dilatation catheter until the balloon 2 reaches a position facing the stenosis.

What is claimed is:

1. An over-the-wire dilatation catheter, for introduction into a body canal of the type comprising:
    a flexible tubular body comprising a distal part, an intermediate part and a proximal part, and having:
    a radially deformable portion forming a balloon disposed at the level of the distal part of the tubular body;
    a first inner duct fluidly connected to the balloon, in liquidtight manner, and connected at the other end to a fluid supply source in order to enable inflating and deflating of the balloon;
    a second inner duct, which does not communicate with said first inner duct, and traverses the body, said second inner duct being defined by a substantially tubular wall and adapted to allow the passage of a guide-wire,
    a core of high modulus of elasticity of which a distal end is embedded in the wall of said second inner duct within said intermediate part of said flexible tubular body,
    wherein the body comprises in its proximal part a two-channel tube constituted of a proximal portion of the second inner duct and of a proximal part of the first inner duct, said core having a proximal section which is contained within the proximal part of the first inner duct,
    wherein the body comprises in a transitional zone located between its proximal part and its intermediate part, a three-channel tube, constituted of:
    a first upper channel extending from the proximal part of the first inner duct and fluidly connected to the intermediate portion of the first inner duct,
    a second lower channel communicating on each side of the transitional zone with, respectively, the proximal and intermediate portions of the second inner duct, and
    a third channel inside which the core is confined, and
    wherein the body comprises, in its intermediate part, an outer tube that extends from the radially deformable balloon-forming portion of the distal part and that coaxially surrounds the intermediate part of the second inner duct while providing an annular space which forms the intermediate part of the first inner duct.

2. The over-the-wire dilatation catheter as claimed in claim 1, wherein the proximal part of the first inner duct is substantially semi-cylindrical in shape.

3. The over-the-wire dilatation catheter as claimed in claim 1, wherein the proximal part of the second inner duct is eccentrically positioned within the proximal part of the flexible tubular body.

4. The over-the-wire dilatation catheter as claimed in claim 1, wherein the proximal part of the first inner duct is substantially semi-cylindrical in shape and wherein the proximal part of the second inner duct is eccentrically positioned within the proximal part of the flexible tubular body.

5. The over-the-wire dilatation catheter as claimed in claim 1, wherein the outer tube is fixed at its proximal end to the three-channel tube and to the two-channel tube.

6. The over-the-wire dilatation catheter as claimed in claim 1, wherein said core has a cross-section that reduces from its proximal end to its distal end.

7. The over-the-wire dilatation catheter as claimed in claim 1, wherein said core is metal.

8. The over-the-wire dilatation catheter as claimed in claim 1, wherein said core extends in the intermediate part up to a point situated immediately proximal to the balloon-forming portion.

9. The over-the-wire dilatation catheter as claimed in claim 1, wherein said over-the-wire dilatation catheter is configured for introduction into a blood vessel.

10. The over-the-wire dilatation catheter as claimed in claim 1, wherein said core is steel.

11. An over-the-wire dilatation catheter for introduction into a body canal, the catheter comprising:
    a flexible tubular body having a distal part, an intermediate part, a transition zone and a proximal part;
    an inflatable balloon mounted on the distal part of the flexible tubular body;
    a first lumen within the flexible tubular body, the first lumen having a distal end fluidly connected to the balloon, an intermediate portion defined by an outer tube extending proximally from the balloon, a transition portion defined by a first channel within the transition zone of the flexible tubular body, a proximal portion defined by a continuation of the first channel within the proximal part of the flexible tubular body, and a proximal end adapted for connection to a fluid supply source for inflating and deflating the balloon;

a second lumen within the flexible tubular body adapted to allow passage of a guide-wire, the second lumen having an open distal end, a distal portion defined by an inner tube within the distal part of the flexible tubular body, an intermediate portion defined by a continuation of the inner tube through the intermediate part of the flexible tubular body and coaxially received within the outer tube, a transition portion defined by a second channel within the transition zone of the flexible tubular body, a proximal portion defined by a continuation of the second channel within the proximal part of the flexible tubular body, and an open proximal end; and a core of high modulus of elasticity having a proximal portion residing within the proximal portion of the first lumen, a transition portion residing within a third channel within the transition zone of the flexible tubular body, and an intermediate portion and a distal end embedded within a wall of the inner tube within the intermediate part of the flexible tubular body.

12. The over-the-wire dilatation catheter of claim 11, wherein the proximal portion of the first lumen is substantially semi-cylindrical in shape and wherein the proximal portion of the second lumen is eccentrically positioned within the proximal part of the flexible tubular body.

13. The over-the-wire dilatation catheter of claim 11, wherein a proximal end of the outer tube is attached to the transition zone and to the proximal part of the flexible tubular body.

14. The over-the-wire dilatation catheter of claim 11, wherein the core has a cross-section that reduces from its proximal end to its distal end.

15. The over-the-wire dilatation catheter of claim 11, wherein the core is made of a metal.

16. An over-the-wire dilatation catheter for introduction into a body canal, said catheter comprising:

a catheter body having a one-channel distal part, a one-channel intermediate part, a three-channel transition zone and a two-channel proximal part;

an inflatable balloon mounted on the distal part of the catheter body;

an outer tube extending proximally from the balloon, the outer tube coaxially surrounding the intermediate part of the catheter body and having a proximal end attached to the catheter body at a point proximal to the intermediate part;

a first lumen within the catheter body, the first lumen having a distal end fluidly connected to the balloon via an annular space between the outer tube and the catheter body, a transition portion defined by a first channel within the three-channel transition zone of the catheter body, a proximal portion defined by a continuation of the first channel within the two-channel proximal part of the catheter body;

a second lumen within the catheter body adapted to allow passage of a guide-wire, the second lumen having an open distal end, a distal portion defined by a guide-wire channel within the one-channel distal part of the catheter body, an intermediate portion defined by a continuation of the guide-wire channel through the one-channel intermediate part of the catheter body, a transition portion defined by a continuation of the guide-wire channel through the three-channel transition zone of the catheter body, and a proximal portion defined by a continuation of the guide-wire channel within the two-channel proximal part of the catheter body, and an open proximal end; and a core of high modulus of elasticity having a proximal portion residing within the proximal portion of the first lumen, a transition portion residing within a third channel within the three-channel transition zone of the catheter body, and an intermediate portion and a distal end embedded within a wall of the one-channel intermediate part of the catheter body.

17. The over-the-wire dilatation catheter of claim 16, wherein the proximal portion of the first lumen is substantially semi-cylindrical in shape and wherein the proximal portion of the second lumen is eccentrically positioned within the proximal part of the catheter body.

18. The over-the-wire dilatation catheter of claim 16, wherein the proximal end of the outer tube is attached to the three-channel transition zone and to the two-channel proximal part of the catheter body.

19. The over-the-wire dilatation catheter of claim 16, wherein the core has a cross-section that reduces from its proximal end to its distal end.

20. The over-the-wire dilatation catheter of claim 16, wherein the core is made of a metal.

* * * * *